(12) United States Patent
Casara et al.

(10) Patent No.: US 9,669,360 B2
(45) Date of Patent: Jun. 6, 2017

(54) METHOD FOR THE SEPARATION OF AMMONIA AND CARBON DIOXIDE FROM AQUEOUS SOLUTIONS

(71) Applicant: SAIPEM S.p.A, San Donato Milanese (MI) (IT)

(72) Inventors: Paolo Casara, San Donato Milanese (IT); Alessandro Gianazza, Legnano (IT)

(73) Assignee: SAIPEM S.p.A., San Donato Milanese (IT)

( * ) Notice: Subject to any disclaimer, the term of this patent is extended or adjusted under 35 U.S.C. 154(b) by 0 days.

(21) Appl. No.: 14/960,662

(22) Filed: Dec. 7, 2015

(65) Prior Publication Data

US 2016/0082394 A1  Mar. 24, 2016

Related U.S. Application Data

(63) Continuation of application No. 13/395,262, filed as application No. PCT/EP2010/005609 on Sep. 1, 2010, now Pat. No. 9,266,745.

(30) Foreign Application Priority Data

Sep. 9, 2009  (IT) ............... MI2009A1551

(51) Int. Cl.
*C02F 1/02* (2006.01)
*B01D 3/02* (2006.01)
(Continued)

(52) U.S. Cl.
CPC ............. *B01D 61/364* (2013.01); *C01C 1/10* (2013.01); *C02F 1/447* (2013.01); *C07C 273/04* (2013.01);
(Continued)

(58) Field of Classification Search
CPC ............ B01D 61/364; B01D 61/362; B01D 2311/04; B01D 69/02; B01D 2313/38;
(Continued)

(56) References Cited

U.S. PATENT DOCUMENTS 4,424,072 A    1/1984 Lerner
5,053,538 A *  10/1991 Linton ............. C07C 273/16
                                            564/65
(Continued)

FOREIGN PATENT DOCUMENTS

DE    295 10 582    10/1995
EP    1 925 355      5/2008
(Continued)

OTHER PUBLICATIONS

Qin, Y., et al., "Hollow Fiber Supported Liquid Membrane Process for the Separation of $NH_3$ from Aqueous Media Containing $NH_3$ and $CO_2$," Journal of Chemical Technology and Biotechnology, vol. 65, No. 2, pp. 137-148, (Feb. 1996).
(Continued)

*Primary Examiner* — Ana Fortuna
(74) *Attorney, Agent, or Firm* — Oblon, McClelland, Maier & Neustadt, L.L.P.

(57) ABSTRACT

The present invention relates to a method for contemporaneously recovering ammonia and carbon dioxide from an aqueous solution thereof, possibly comprising their condensates, in a synthesis process of urea, characterized in that it comprises a hydrophobic microporous membrane distillation phase of an aqueous solution comprising ammonia, carbon dioxide and their saline compounds or condensates, said distillation being carried out at a temperature ranging from 50 to 250° C. and a pressure ranging from 50 KPa to 20 MPa absolute, with the formation of a residual aqueous solution, possibly comprising urea, and a gaseous permeate
(Continued)

stream, comprising ammonia, carbon dioxide and water. The present invention also relates to an apparatus for effecting the above method and a production process of urea which comprises the above method.

7 Claims, 4 Drawing Sheets (51) Int. Cl.
  B01D 3/14     (2006.01)
  B01D 35/18    (2006.01)
  B01D 61/36    (2006.01)
  C01C 1/10     (2006.01)
  C07C 273/04   (2006.01)
  C02F 1/04     (2006.01)
  C02F 1/44     (2006.01)
  C02F 101/10   (2006.01)
  C02F 101/16   (2006.01)
  C02F 103/36   (2006.01)

(52) U.S. Cl.
  CPC ............ B01D 2313/22 (2013.01); C02F 1/04 (2013.01); C02F 1/44 (2013.01); C02F 2101/10 (2013.01); C02F 2101/16 (2013.01); C02F 2103/36 (2013.01)

(58) Field of Classification Search
  CPC ...... B01D 2325/38; B01D 63/02; B01D 3/40; B01D 5/009
  See application file for complete search history.

(56) References Cited

U.S. PATENT DOCUMENTS

| | | | | |
|---|---|---|---|---|
| 5,256,296 A * | 10/1993 | Baker | ................. | B01D 53/226 210/321.6 |
| 5,670,053 A | 9/1997 | Collentro et al. | | |
| 5,749,941 A | 5/1998 | Jansen et al. | | |
| 5,766,479 A | 6/1998 | Collentro et al. | | |
| 6,086,768 A * | 7/2000 | Sims | ................. | B01D 17/00 210/634 |
| 6,538,157 B1 | 3/2003 | Goorden et al. | | |
| 7,381,858 B2 * | 6/2008 | Huff, Jr. | ................. | C07C 7/144 585/321 |
| 7,871,520 B2 * | 1/2011 | Ma | ................. | B01D 3/06 203/10 |
| 8,106,241 B2 | 1/2012 | Carlessi et al. | | |
| 8,293,201 B2 | 10/2012 | Casara et al. | | |
| 8,758,485 B2 * | 6/2014 | Casara | ................. | B01D 53/1425 423/237 |
| 8,814,988 B2 * | 8/2014 | Casara | ................. | B01D 53/58 95/178 |
| 8,927,770 B2 | 1/2015 | Carlessi et al. | | |
| 9,199,926 B2 * | 12/2015 | Carlessi | ................. | C07C 273/04 |
| 9,266,745 B2 * | 2/2016 | Casara | ................. | B01D 61/364 |
| 2002/0014154 A1 | 2/2002 | Witzko et al. | | |
| 2009/0152199 A1 * | 6/2009 | Ma | ................. | B01D 3/06 210/640 |
| 2010/0072135 A1 * | 3/2010 | Hanemaaijer | ................. | B01D 1/0035 210/640 |
| 2010/0122784 A1 * | 5/2010 | Jemaa | ................. | C02F 1/20 162/14 |
| 2012/0039787 A1 | 2/2012 | Casara et al. | | |
| 2012/0067209 A1 | 3/2012 | Sandru et al. | | |
| 2012/0228225 A1 | 9/2012 | Casara et al. | | |

FOREIGN PATENT DOCUMENTS

| | | | | |
|---|---|---|---|---|
| EP | 2386346 | | 11/2010 | |
| WO | 89 01468 | | 2/1989 | |
| WO | WO 95/26225 | | 5/1995 | |
| WO | 01 04085 | | 1/2001 | |
| WO | WO 2010/081707 | * | 7/2010 | ............. B01D 53/14 |

OTHER PUBLICATIONS

International Search Report Issued Nov. 30, 2010 in PCT/EP10/05609 Filed Sep. 1, 2010.

* cited by examiner

METHOD FOR THE SEPARATION OF AMMONIA AND CARBON DIOXIDE FROM AQUEOUS SOLUTIONS

CROSS REFERENCE TO RELATED APPLICATIONS

This application is a continuation of U.S. patent application Ser. No. 13/395,262, filed on Apr. 26, 2012, Now U.S. Pat. No. 9,266,745, the text of which is incorporated herein by reference and which is a 35 U.S.C. §371 national stage patent application of international patent application PCT/EP10/05609, filed on Sep. 1, 2010, the text of which is incorporated herein by reference, and claims the benefit of the Italian patent application MI2009A 001551, filed Sep. 9, 2009, the text of which is also incorporated herein by reference.

The present invention relates to a method for separating ammonia and carbon dioxide from aqueous solutions.

In particular, the present invention relates to a method for contemporaneously recovering ammonia ($NH_3$) and carbon dioxide ($CO_2$) from an aqueous solution comprising ammonia, carbon dioxide and saline compounds or condensates of ammonia and carbon dioxide and possibly urea.

The need is felt for improving methods for the separation and recovery of $NH_3$ and $CO_2$ to be used, in particular, in synthesis processes of urea, considering the high commercial value of $NH_3$, and also for optimizing a production cycle in which $NH_3$ and $CO_2$ are used as raw materials.

The synthesis of urea is effected by the reaction of ammonia and carbon dioxide at high pressure and temperature, the subsequent separation of the urea from the mixture containing the non-reacted products and recycling of the same to the synthesis reactor.

All industrial processes for the preparation of urea are based on direct synthesis according to the following reaction:

$$2NH_3 + CO_2 \leftrightarrow CO(NH_2)_2 + H_2O \qquad (A)$$

This synthesis takes place in two distinct reaction steps:

$$NH_3 + CO_2 \leftrightarrow (NH_2)COONH_4 \qquad (A')$$

$$(NH_2)COONH_4 \leftrightarrow CO(NH_2)_2 + H_2O \qquad (A'')$$

In the first step (A') an exothermic equilibrium reaction takes place having a high reaction rate at room temperature, which however, at the high temperatures required by step (A''), requires high pressures to reach a favourable equilibrium.

In the second step (A'') an endothermic reaction takes place, which only reaches a significant rate at high temperatures (>150° C.), with an equilibrium state which, at 185° C., starting from a mixture of reagents in a stoichiometric ratio, leads to a $CO_2$ conversion slightly higher than about 50%. This unsatisfactory conversion can be conveniently increased by raising the $NH_3/CO_2$ ratio.

Processes for the production of urea by direct synthesis starting from ammonia and carbon dioxide have been widely illustrated and described in the specific literature of the field. A wide review of the most common processes for the production of urea can be found, for example, in "Encyclopedia of Chemical Technology" Ed. Kirk-Othmer, Wiley Interscience, fourth ed. (1998), Supplement, pages 597-621.

Industrial processes for the production of urea normally carry out the synthesis in a reactor fed with $NH_3$, $CO_2$ and aqueous solutions of ammonium carbonate and/or carbamate coming from the recycled streams of the non-converted reagents, at temperatures ranging from 150 to 215° C., at pressures of at least 13 MPa, with a $NH_3/CO_2$ molar ratio of between 2.5 and 5, calculated with respect to the sum of the feeding streams, including ammonia in the form of ammonium salt. In addition to the water formed and excess $NH_3$ fed, the reactor effluent still contains considerable quantities of $CO_2$, mainly in the form of non-converted ammonium carbamate.

In order to maximize the yield of the synthesis process of urea, as explained in greater detail hereunder, the free ammonia, water and ammonium carbamate contained in the effluent leaving the synthesis reactor, are separated in a series of subsequent purification steps to obtain urea containing the minimum possible quantity of reaction by-products, in particular ammonium carbamate and water. Finally, the urea, in a suitable, degree of purity, is solidified into granular form.

The ammonium carbamate is removed from the effluent leaving the synthesis reactor by decomposition of the carbamate under suitable temperature and pressure conditions. The ammonium carbamate is typically decomposed into ammonia and carbon dioxide by feeding the reaction effluent to a high-pressure decomposer (also called stripper), substantially operating at the same pressure as the synthesis reactor and at a slightly higher temperature. The stripper consists of a tube-bundle exchanger arranged vertically, in which the effluent, leaving the reactor, containing, in addition to urea, non-reacted carbamate and ammonia in excess, is passed in a thin layer (film) along the inside of the tubes, whereas steam saturated at a pressure of about 23 MPa is circulated and condensed in the chamber outside the tube bundle, to supply the energy necessary for the decomposition of the carbamate and removal of the excess ammonia. In the state of the art, the stripper is also called falling film tube-bundle heat exchanger.

The gaseous ammonia, which is separated from the urea solution in the stripper, leaves the stripper entraining with it the decomposition products (so-called self-stripping). Alternatively, the stripping of the decomposition products can be effected with inert gases or with ammonia, carbon dioxide or mixtures thereof, specifically introduced into the stripper.

The liquid effluent leaving the high-pressure decomposer is an aqueous solution of urea which, however, still contains a significant quantity of carbamate and dissolved ammonia. In order to separate these compounds from the urea and recover them within the process, the aqueous solution leaving the high-pressure decomposer is fed to a second decomposer (medium-pressure decomposer) which operates at about 2 MPa and about 160° C. The heat necessary for the decomposition of the carbamate in this step is supplied by medium-pressure steam (4-5 MPa) or by recirculating the gaseous stream containing ammonia and ammonium carbamate leaving the high-pressure decomposer.

The aqueous solution of urea leaving the medium-pressure decomposer is subjected to a further purification step, feeding it to a third decomposer (low-pressure decomposer) which operates at about 4 bar and about 140° C. Analogously to the case of the high and medium pressure decomposers, also in this case, the necessary heat is supplied by means of medium-pressure steam or by the recycling of one or more hot gaseous streams coming from other steps of the process.

In the final section of the production plant, downstream of the decomposition sections, the aqueous solution of purified urea obtained from the last decomposer is solidified into granular form in suitable granulators or prilling towers by cooling with air.

The gaseous streams leaving the various decomposition steps (high, medium and low pressure) and containing ammonia and carbon dioxide are condensed in suitable equipment, forming liquid streams containing ammonia, carbon dioxide (prevalently in the form of ammonium carbamate) and water, which are recycled to the synthesis reactor.

If, on the one hand, the recycling of these streams increases the conversion efficiency of the raw materials consisting of ammonia and carbon dioxide, on the other, it implies the re-introduction of water into the process which, considering the stoichiometry of the overall synthesis reaction (A), significantly lowers the yield of the urea synthesis reaction.

It is therefore evident that in processes of the type described above, in order to maximize the yield of the urea synthesis reaction, it is of fundamental importance to be able to effectively and selectively separate the ammonia and carbon dioxide from the aqueous solutions containing them, in order to recycle streams containing the lowest possible quantity of water to the process (in particular, to the synthesis reactor).

The use of the decomposers described above, as also that of other separation systems used in the state of the art (for example distillation columns), allows ammonia and carbon dioxide to be recovered separately, at a high degree of purity. The production of pure compounds, however, leads to a high energy consumption which is significantly reflected on the overall urea production costs.

It is also known that the separation of ammonia and carbon dioxide by the distillation of liquid streams which circulate in a production plant of urea can be affected by the formation of solid crystals in the distillation unit, whose removal would require washing the unit with water or another solvent with a consequent reduction in the distillation efficiency.

An objective of the present invention is to overcome the drawbacks of the known art.

A first object of the present invention relates to a method for contemporaneously recovering ammonia and carbon dioxide from an aqueous solution thereof, possibly comprising their condensates, in a synthesis process of urea, characterized in that it comprises a distillation on a hydrophobic microporous membrane phase of an aqueous solution comprising ammonia, carbon dioxide and their saline compounds or condensates, said distillation being carried out at a temperature ranging from 50 to 250° C. and a pressure ranging from 50 KPa to 20 MPa absolute, with the formation of a residual aqueous solution, possibly comprising urea, and a gaseous permeate stream, comprising ammonia, carbon dioxide and water.

An object of the present invention also relates to an apparatus for effecting the above method, comprising:
  a unit for subjecting an aqueous solution comprising ammonia, carbon dioxide and their saline compounds or condensates, to distillation on a hydrophobic microporous membrane, with the formation of a residual aqueous solution and a gaseous permeate stream, comprising ammonia, carbon dioxide and water;
  heating means of the aqueous solution comprising ammonia, carbon dioxide and their saline compounds or condensates.

A further object of the present invention relates to a process for the production of urea comprising a contemporaneous recovery phase of ammonia and carbon dioxide from an aqueous solution thereof, possibly comprising their condensates, by means of distillation on a hydrophobic microporous membrane of an aqueous solution comprising ammonia, carbon dioxide and their saline compounds or condensates, with the formation of a residual aqueous solution and a gaseous permeate stream, comprising ammonia, carbon dioxide and water.

In the description of the invention, object of the present patent application, reference is made to the following figures.

The Applicant has surprisingly found that with the process, object of the present invention, based on the use of distillation on a microporous membrane, it is possible to improve the overall conversion yield of a synthesis process of urea, at the same time reducing its energy consumption. The distillation on a microporous membrane, in fact, allows gaseous streams comprising ammonia, carbon dioxide and small quantities of water (in the form of vapour) to be effectively recovered from aqueous solutions which circulate in this process, without the undesired formation of solids and with an overall reduced energy consumption.

The distillation on a microporous membrane is a technique used in the state of the art for separating gaseous compounds from solutions in water or in organic solvents. The use of this technique however is not known for the treatment of solutions produced within a synthesis process of urea.

In distillation on a membrane, a liquid phase and a gaseous phase are put in contact with the two opposite sides of a hydrophobic microporous membrane. The contact between the two phases through the pores of the membrane allows a controlled mass transfer of the chemical species present therein, avoiding the dispersion of one phase within the other.

The driving force of the diffusion of a chemical species from the fluid which flows on one side of the membrane (feeding stream) to that flowing on the opposite side (gaseous permeate stream or carrier stream) is the temperature, concentration and pressure gradient existing between the two fluids.

Thanks to the high porosity of the membrane, this type of distillation process operates with a contact surface between the two fluids which can be much higher with respect to that of a traditional distillation, with obvious advantages from the point of view productivity and reduction in the encumbrance of the equipment used.

The method object of the present invention uses the distillation on a hydrophobic microporous membrane technique for contemporaneously recovering ammonia and carbon dioxide from aqueous solutions in a urea production process. These solutions contain, in addition to water, ammonia and carbon dioxide in the form of dissolved gases or in the form of saline compounds or condensates, such as for example ammonium carbamate and/or ammonium carbonate.

The method object of the present invention is preferably applied to the contemporaneous recovery of ammonia and carbon dioxide from recycled aqueous solutions in a urea production process. The recycled aqueous solutions are the liquid streams generated in various steps of a urea production process comprising ammonia, carbon dioxide and their salts or condensates, which can be advantageously re-fed to the synthesis reactor or to other steps of the same process in order to maximize the yield.

In a second preferred embodiment, the method object of the present invention can also be used for treating solutions comprising ammonia, carbon dioxide, water and urea, such as, for example the reaction effluent leaving the synthesis reactor of the urea production process or solutions of urea leaving the various carbamate decomposition steps within the same process.

Considering the operating temperature and pressure conditions adopted in a production process of urea, the term "residual aqueous solution" used with reference to the method object of the present invention refers to the prevalently liquid phase which remains at the end of the membrane distillation, after the removal by evaporation of part of the species contained therein. The term "gaseous permeate stream", on the other hand, refers to the streams or mixtures in which the liquid phase is substantially absent, due to the removal by evaporation of part of the species present in the aqueous solution subjected to distillation, regardless of their effective physical state.

In this case, the distillation on a hydrophobic microporous membrane units represent a valid alternative to the tube-bundle decomposers typically used in the high-pressure stripping step.

The above aqueous solutions which can be treated according to the present invention comprise ammonia, carbon dioxide, water and possibly urea in varying ratios, depending on the step of the urea process in which they are produced. The above solutions preferably comprise a quantity ranging from 20 to 70% by weight of ammonia, a quantity ranging from 10 to 60% by weight of carbon dioxide, a quantity ranging from 10 to 70% by weight of water and, possibly, a quantity ranging from 0 to 60% by weight of urea.

More preferably, the above solutions preferably comprise a quantity ranging from 20 to 60% by weight of ammonia, a quantity ranging from 10 to 50% by weight of carbon dioxide, a quantity ranging from 10 to 60% by weight of water and, possibly, a quantity ranging from 0 to 50% by weight of urea.

The above weight percentages refer to the overall weight of ammonia or carbon dioxide present in the solution in free form, in the form of a salt or condensate.

The method, object of the present invention, gives the best results when applied to aqueous solutions which form a contact angle (static) with the material of the membrane equal to or greater than 90°, preferably greater than 120°. The measurement of the contact angle is effected with the known sessile drop method and is normally carried out using automatic optical equipment (goniometers), commercially available, which effect the measurement of the angle formed by a microdrop (a few μL) deposited on the surface of the solid material (membrane). The value of the angle 20 seconds after the depositing of the drop is considered the measurement of the static contact angle.

In accordance with the present invention, the distillation on a hydrophobic microporous membrane is preferably carried out at a temperature ranging from 50 to 250° C. and a pressure ranging from 50 KPa to 20 MPa absolute. Under these conditions, the passage takes place of the species $CO_2$ and $NH_3$ present in the aqueous solution and water vapour through the pores of the membrane, in the form of vapour. The quantity of water vapour in the gaseous permeate stream is in any case reduced with respect to that present in a stream obtained with traditional distillation systems. Due to the passage of $NH_3$ and $CO_2$ through the membrane, there is a progressive enrichment of the gaseous permeate stream which flows on the side of the membrane opposite to that of the aqueous solution and, contemporaneously, the progressive reduction in the concentration of the species present in the latter (purified aqueous solution).

The temperature and pressure conditions of the distillation are selected in relation to the characteristics of the aqueous solution to be treated.

The distillation is preferably carried out at a temperature ranging from 80 to 220° C., more preferably from 110 to 190° C., whereas the pressure preferably ranges from 0.15 to 18 MPa absolute, more preferably from 0.5 to 16 MPa absolute.

During the membrane distillation, the pressure of the gaseous stream comprising $NH_3$ and $CO_2$, which flows on one side of the membrane (vapour side), must be kept at a value lower than or equal to the pressure of the solution to be treated which flows on the opposite side (liquid side). Furthermore, the difference between the pressure of the liquid side and that of the vapour side is preferably as high as possible, but must be lower than the minimum pressure difference which would lead to the passage of the solvent in liquid phase through the pores of the membrane (flooding), and to the subsequent mixing of the same with the gaseous stream comprising $NH_3$ and $CO_2$. This minimum pressure difference is defined as critical pressure and can be easily determined by an expert in the field on the basis of the characteristics of the process fluids and material forming the membrane, by possibly carrying out a few tests and preliminary experimental measurements.

The critical pressure of the solution subjected to distillation is variable and depends not only on the wettability characteristics of the processed solution (contact angle with the material forming the membrane), but also on the construction characteristics of the membrane and type of material of which the latter is composed. Critical pressures suitable for effecting the membrane distillation step according to the present invention are preferably greater than 50 KPa.

The microporous membrane distillation process is preferably carried out with devices known in the state of the art as membrane contactors. Membrane contactors (hereinafter indicated with the abbreviation "MC") comprise any form of hydrophobic microporous membranes, such as, for example, hollow fibres, flat membranes, spiral wound membranes, etc.

Figure 1:
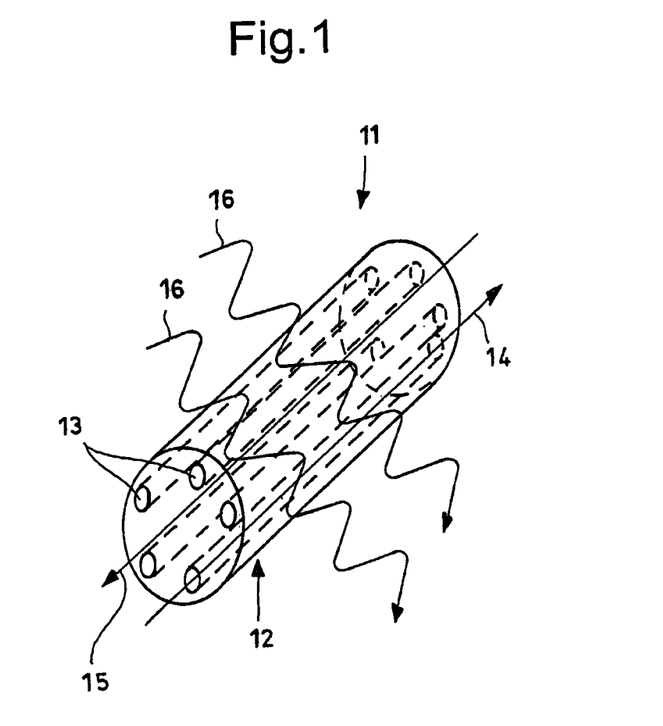
FIG. 1: schematic representation of a device for distillation on a hydrophobic microporous membrane which can be used for effecting the method object of the present invention.

A possible preferred embodiment of an MC device is illustrated in FIG. 1.

With reference to FIG. 1, the MC device 11 which can be used for the purposes of the present invention consists of an apparatus comprising an outer casing consisting of a cylindrical mantle 12, preferably arranged in a horizontal position during the distillation process, inside which a series of tubular elements 13 are aligned, consisting of cylindrically-shaped hydrophobic microporous membranes (hollow fibres), connected at the ends with a distribution chamber and a collection chamber (the chambers are not shown in FIG. 1). The aqueous solution to be treated for recovering ammonia and carbon dioxide contained therein is preferably passed outside the tubular elements 13, i.e. in the space between said tubular elements 13 and the cylindrical mantle 12, according to the flow direction indicated by the arrow 15. In this preferred case, the ammonia and carbon dioxide vapours and water vapour are released, through the membranes, into the space inside the same, and are then collected through a single outlet according to the flow direction indicated by the arrow 14.

The pressure differential between the aqueous solution flowing outside the tubular elements 13 and the vapours flowing in the opposite direction inside the tubular elements 13 is conveniently maintained at a value ranging from 40 to 150 KPa and is in any case lower than the critical pressure which represents the wettability limit of the pores, in order to avoid the pore wetting phenomenon. As already mentioned, the critical pressure value depends on the material of which the membrane is composed and the kind of solution. In order to better sustain the pressure differential, the microporous membranes can possibly be supported with a rigid material permeable to vapours (not shown in FIG. 1), which, in the above preferred case, consists of a hollow tube on which the membranes are wound, whereas it can be a tube containing the membranes in its interior, if the aqueous solution is passed inside the tubular elements 13 of the MC device 11.

In the embodiment illustrated in FIG. 1, the flow of aqueous solution is in countercurrent with respect to that of the gaseous permeate stream. In the method according to the present invention, however, the two streams can also flow concurrently. Furthermore, the method can also be applied in batch mode.

Heat can be supplied to the device 11, for example by means of medium- or high-pressure steam, which passes through a tube bundle or heating chamber (not shown in the figure) subsequently exiting from the device 11 in a condensate phase. More conveniently, however, the necessary heat can be provided by suitably irradiating the aqueous solution in contact with the microporous membranes with a beam of microwaves 16 at a frequency within the range of 2,300 to 2,700 MHz, preferably from 2,400 to 2,600 MHz. The most suitable frequencies for an optimum, absorption of the polar molecules present in the solution treated can be easily selected by an expert in the field in relation to the composition and temperature of the solution, on the basis of the absorption characteristics specified in literature or simple preliminary scanning tests. In this case, the rigid materials of which the apparatus is composed (cylindrical mantle 12 and possible cylindrical supports made of a material permeable to vapours), must be selected from those transparent to microwaves within the frequency range used.

The microporous membrane distillation is preferably effected under self-stripping conditions, i.e. in the absence of an additional carrier stream. In order to obtain a greater extraction of $CO_2$ and $NH_3$, a stream of $CO_2$ and/or $NH_3$, and possibly a stream of inert gas can be preferably used as carrier stream, maintained at a pressure close to, but lower than, that of the aqueous solution treated (feeding stream).

The membranes used for the purposes of the present invention typically consist of materials based on hydrophobic polymers, which form a contact angle $\geq 90°$, preferably $\geq 120°$ with the processed solutions, as previously specified. In a first approximation, for the purposes of the present invention, the hydrophobicity of the membranes can be evaluated on the basis of these criteria applied to the measurement of the contact angle with water, rather than with the process solution.

Examples of suitable materials for forming the membranes are fluorinated polymers and copolymers, such as polytetrafluoroethylene (PTFE), polyvinylidenefluoride or Nation®, certain polyolefins with a high crystallinity, such as isotactic polypropylene, polyacrylonitrile, polysulfones. These materials offer a high thermal resistance (up to 220-250° C.), and a high chemical and mechanical resistance. The maximum pressure difference which can be sustained by these membranes is about 100 KPa. This kind of membrane is commercially available.

In a preferred embodiment, the distillation on membrane is carried out in distillation units containing two or more MC devices of the type described above which can operate under different temperature and pressure conditions.

In the process according to the present invention, the distillation temperature is preferably maintained at 50 to 250° C. by irradiation with electromagnetic radiations having a frequency within the microwave range. Even more preferably, the irradiation of the aqueous solution is effected so that the temperature of the aqueous solution increases along the flow direction of the feeding stream, i.e. lower at the inlet of the MC device containing the membrane and higher at the outlet. As the distillation process proceeds, the aqueous solution becomes impoverished in $NH_3$ and $CO_2$ and the liquid-vapour equilibrium conditions become less favourable for the separation of these species from the aqueous solution and their passage through the membrane. Upon heating the aqueous solution to an increasing temperature as it flows in contact with the membrane, the reduced tendency of the ammonia and carbon dioxide to separate from the aqueous solution is compensated, also avoiding the condensation of the vapours of the gaseous permeate stream containing ammonia, carbon dioxide and water in the vapour side.

The heating can be effected with microwave generation devices known in the state of the art. The use of microwaves offers the advantage of being able to selectively heat only the molecules of water, $NH_3$, $CO_2$ and other polar molecules in the liquid state, avoiding a significant heating of those present in vapour form. This enables thermal energy to be supplied to the feeding stream, favouring the subsequent permeation of gaseous $NH_3$ and $CO_2$ through the membrane.

Furthermore, the use of microwaves also prevents the flooding of the pores of the membrane, i.e. the penetration into the pores of the solvent (water) of the aqueous solution in liquid form. Should flooding of the pores occur due to an overpressure on the side of the membrane in which the solution to be treated flows, the selective heating of the molecules of liquid water on the part of the microwaves allows the liquid water which has penetrated inside the pores, to evaporate, thus regenerating the membrane in situ without interrupting the functioning of the equipment and avoiding the application of counterpressures.

Furthermore, it has been found that the use of microwaves for heating the liquid has the further advantage of favouring the dispersion of the ammonia and carbon dioxide in the possible gaseous carrier stream, without causing its undesired heating and increasing the energy consumption.

In order to supply heat by irradiation with microwaves, MC devices must be used in which the outer casing consists of materials transparent to microwaves, for example materials such as PTFE, glass, Pyrex, etc.

Heating by means of microwaves is not only easy to apply but also allows the thermal energy supplied to the membrane distillation device to be accurately modulated. Microwave heating devices, moreover, having conversion efficiencies of electric energy into microwaves in the order of about 70%, contribute to obtaining an overall higher energy yield of the recovery process of ammonia and carbon dioxide.

Although heating with the use of microwaves is preferred for the advantages described above, the heating of the aqueous solution can also be effected with the conventional techniques, for example by passing the aqueous solution in a heat exchanger, before subjecting it to distillation on membrane.

The main operating parameters which influence the distillation on membrane according to the method, object of the present invention, are the flow rate and pressure of the aqueous solution in contact with the membrane, the flow rate and pressure of the gaseous permeate stream and possible additional carrier stream, as well as the temperature gradient obtained in the aqueous solution by irradiation with microwaves. The degree of influence on the effectiveness of the method of each of the above operating parameters can be evaluated experimentally. Optimum operating conditions are obtained when the flow rate of the aqueous solution and its pressure on the surface of the membrane is such as to compensate the pressure drop due to the passage through the membrane of the gaseous species leaving the aqueous solution.

The distillation on membrane of an aqueous solution containing ammonia, carbon dioxide and water according to the method, object of the present invention, returns a gaseous permeate stream and a purified aqueous solution having variable characteristics in relation to the composition of the solution treated and operating conditions at which the distillation on membrane is effected. The distillation of solutions comprising ammonia, for example, in a quantity ranging from 5 to 40%, preferably from 10 to 40% by weight, carbon dioxide in a quantity ranging from 2.5 to 20%, preferably from 5 to 20% by weight and urea in a quantity ranging from 10 to 60%, preferably from 20 to 40% by weight, effected at a temperature ranging from 100 to 220° C. and a pressure ranging from 10 to 18 MPa, produces a purified aqueous solution having a residual ammonia content ranging from 1 to 30% by weight, carbon dioxide ranging from 1 to 10% by weight, urea in a quantity ranging from 20 to 60%, preferably from 30 to 60%, by weight.

According to a different aspect of the process of the present invention, relating to the concentration of recycled solutions without urea and comprising ammonia in a quantity ranging from 5 to 70%, preferably from 20 to 70% by weight, carbon dioxide in a quantity ranging from 2.5 to 30%, preferably from 10 to 30% by weight, the distillation is carried out at a temperature ranging from 60 to 200° C., preferably from 80 to 180° C. and a pressure ranging from 1 to 10 MPa, a purified aqueous solution is obtained having ammonia and carbon dioxide contents greatly reduced with respect to the initial solution, respectively ranging up to 20% by weight of $NH_3$ and up to 10% by weight of $CO_2$, but preferably lower than 2%, more preferably lower than 1%, by weight.

As the gaseous permeate stream obtained with the method, object of the present invention, substantially consists of $NH_3$ and $CO_2$ and with a low water content, it can be recycled to the urea synthesis reactor, possibly after recovery of the residual heat, or to another production process (for example, in a synthesis process of ammonia).

The gaseous permeate stream can also be subjected to further separation processes to recover $NH_3$ and $CO_2$ separately, with a high degree of purity.

The method according to the present invention allows the contemporaneous recovery of $NH_3$ and $CO_2$ contained in an aqueous solution in a urea production process, allowing the recovery of the above compounds.

The method is therefore characterized by a high energy efficiency and does not have the problems of the undesired formation of solid impurities of the techniques of the state of the art.

The method according to the present invention also has a high energy efficiency, particularly marked in the case of the preferred use of microwaves for the heating of the membrane distillation devices, and by the fact that the ammonia and carbon dioxide can be contemporaneously recovered in a single recyclable gaseous stream (as such, or as a concentrated solution of ammonium carbonate or carbamate, after condensation) to the urea synthesis reactor.

Finally, the process according to the present invention has the following further advantages, with respect to the techniques used in the state of the art deriving from the use of membrane distillation:

a high separation efficiency of the ammonia and carbon dioxide also in diluted solutions, due to the fact that, as the interface surface consists of pores of the membrane, it does not vary with a variation in the flow conditions of the carrier stream and feeding stream;

absence of the formation of emulsions as there is no dispersion phenomenon between the fluids;

absence of corrosion phenomena of the devices used for the distillation on membrane, thanks to the particular type of materials used for the membranes and for the casing of the MC devices;

the fluids in contact with the membrane do not need to have a different density;

the scale-up operations of the membrane distillation processes are simplified, as an increase in the volume of the feeding stream to be treated corresponds to a linear increase in the number of modules (MC devices);

there is no transfer by evaporation of part of the solution to be treated or treated in the gaseous stream containing ammonia and carbon dioxide possibly fed to the urea plant: in this way, the urea plant is not polluted with substances foreign to the process itself;

there are no moving mechanical parts subject to wear or possible breakage;

reduced encumbrance of the equipment necessary for the distillation.

Some application examples to a urea production process are illustrated hereunder to outline the characteristics and advantages of the method of the present invention. The examples are provided for purely illustrative purposes of the present invention and should not be considered as limiting the protection scope defined by the enclosed claims.

EXAMPLE 1 (COMPARATIVE)

Figure 2:
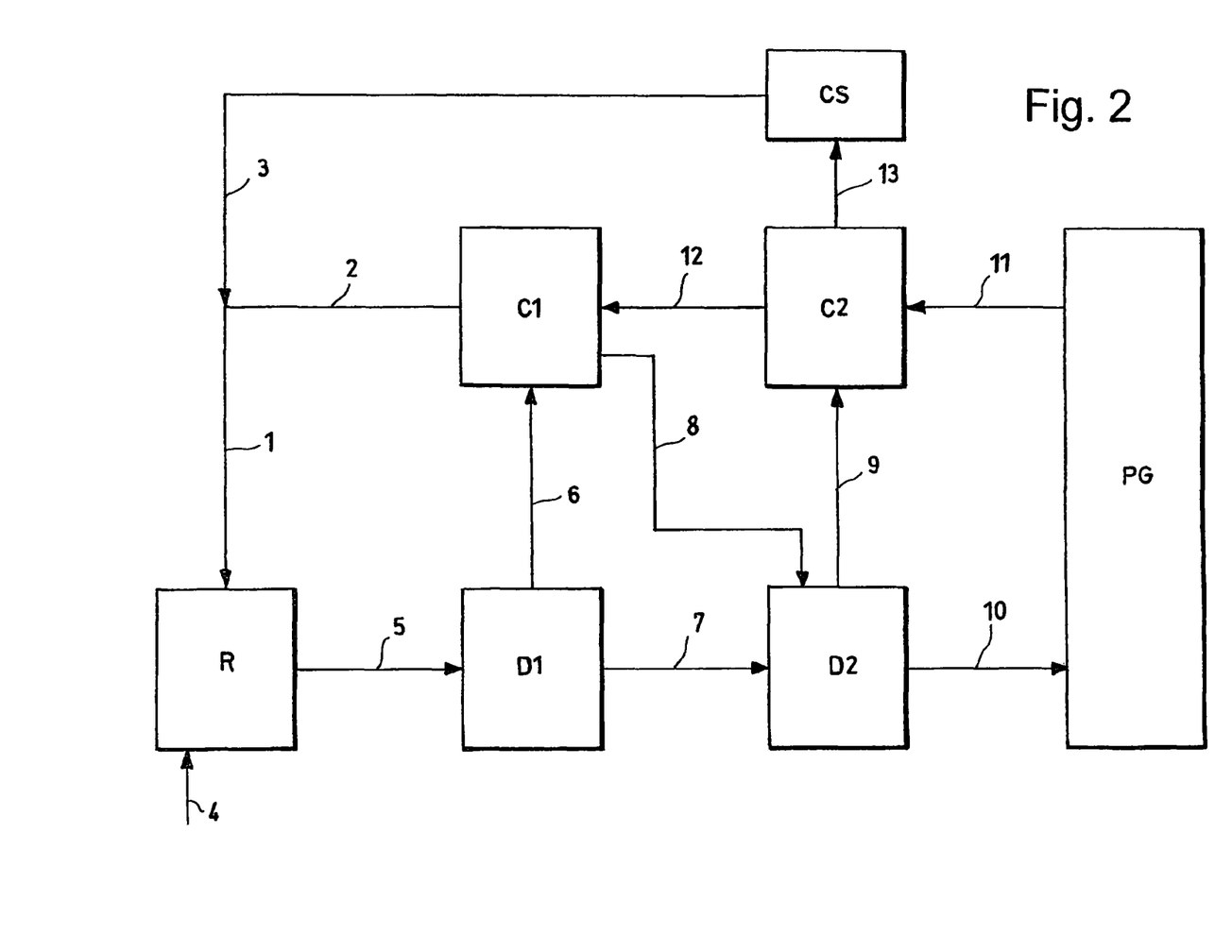
FIG. 2—schematic representation of a urea production process according to the state of the art.

FIG. 2 illustrates a schematic representation of a process for the production of urea according to the state of the art. Particular functions such as pumps, valves, and other equipment not significant for a full understanding of the processes schematized, are not shown in the above FIG. 2.

According to a process known in the state of the art, 2,366 tons/day of a stream 1 of ammonia and ammonia carbamate consisting of 1,564 tons/day of ammonia, 498 tons/day of carbon dioxide and 304 tons/day of water, are fed to a reactor R. The feeding stream 1 is obtained by mixing a recycled stream 2 (1,575 tons/day) consisting of an aqueous solution of ammonium carbamate leaving a high-pressure condenser/separator C1 and a stream 3 of liquid ammonia (790.6 tons/day) substantially pure (99.91% ammonia, 0.09% water) leaving a condensation/storage section CS of ammonia. 736.3 tons/day of a stream 4 of carbon dioxide are also fed to the reactor R. The reactor R operates at a temperature of 187° C. and a pressure of 15.8 MPa (abs).

A liquid stream 5 (reaction effluent) comprising urea, carbon dioxide, water and non-reacted ammonia leaves the reactor R. The reaction effluent (stream 5) is a stream of 3,102 tons/day consisting of 995 tons/day of ammonia, 498 tons/day of carbon dioxide (prevalently in the form of ammonium carbamate), 605 tons/day of water and 1,004 tons/day of urea. The reaction effluent (stream 5) is fed to a first high-pressure decomposer D1 (stripper) consisting of a falling film tube bundle heat exchanger, operating at a temperature of 204° C. and a pressure of 14.7 MPa (abs). The decomposer D1 is heated by feeding a stream of saturated steam (644 tons/day) into the mantle at a pressure of about 2.3 MPa (abs).

In the decomposer D1, the ammonium carbamate is decomposed to ammonia and carbon dioxide, in accordance with the thermodynamic equilibrium which is established under the specific temperature and pressure conditions at which the first decomposer D1 is operating. A gaseous stream 6 (811 tons/day) containing ammonia (432 tons/day), carbon dioxide (337 tons/day) and water vapour (42 tons/day) leaves the head of the first decomposer D1, which is fed to a condenser/separator C1 (high-pressure condenser/separator), operating under substantially isobar conditions with respect to those of the decomposer D1, in order to yield its own residual heat. An aqueous solution of urea 7 (2,291 tons/day) containing ammonia (563 tons/day), carbon dioxide (161 tons/day), water (563 tons/day) and urea (1,004 tons/day), leaves the bottom of the decomposer D1. The non-condensed fraction of the gaseous stream 6 fed to the high-pressure condenser/separator C1 is, on the other hand, separated (stream 8) and fed to a second decomposer D2. The stream 8 (14 tons/day) fed to the second decomposer D2 consists of ammonia (13 tons/day), carbon dioxide (1 ton/day) and is substantially free of water.

The solution of urea 7 leaving the first decomposer D1 is fed to a subsequent decomposition step of the carbamate in the second decomposer D2 (medium-pressure decomposer) which operates at about 160° C. and a pressure of about 2 MPa (abs), with the separation of a gaseous stream 9 (741 tons/day) containing ammonia (475 tons/day), carbon dioxide (131 tons/day) and water vapour (135 tons/day), which is fed to a condenser/absorber C2 (medium-pressure condenser/absorber), for condensation and contemporaneous recovery of the residual heat.

The solution comprising urea leaving the second decomposer D2 (stream 10—1,564 tons/day) consists of ammonia (101 tons/day), carbon dioxide (31 tons/day), water vapour (428 tons/day) and urea (1,004 tons/day). The above stream 10 is fed to the block PG, i.e. the subsequent process sections in which further decomposition phases of the residual carbamate and condensation/separation of the gaseous products are effected, together with the purification and solidification phases to obtain the final solid product consisting of urea in granules and the treatment phase of the wastewater. In the process phases represented by the block PG of FIG. 2, further gaseous and liquid streams are produced, comprising ammonia, carbon dioxide and water, which are recycled to the reactor R. The recycled stream coming from the block PG is represented in FIG. 1 by a stream 11 (252 tons/day) which connects the block PG with the section C2. The above recycled stream 11 contains ammonia (101 tons/day), carbon dioxide (31 tons/day) and water vapour (120 tons/day).

In the section C2, the gaseous stream 9 leaving the second decomposer D2 is partially condensed and joined with the recycled stream 11 coming from the block PG, with the formation of a stream 12 (778.1 tons/day) containing ammonia (355 tons/day), carbon dioxide (162 tons/day) and water (261.1 tons/day). In the section C2, a stream 13 of gaseous ammonia is also separated, which is fed to the condensation/storage section CS of ammonia.

In the section C1, high-pressure condenser/separator, the gaseous stream 6 coming from the decomposer D1 is partially condensed and joined with the stream 12, leaving the section C2, with the formation of a stream 2 (1,575 ton/day) consisting of ammonia (774 tons/day), carbon dioxide (498 tons/day) and water vapour (303 tons/day).

In the process described above, in order to produce 1,004 tons/day of urea, a quantity of saturated steam at 2.3 MPa(abs), equal to 644 tons, was introduced into the decomposer D1. The urea synthesis reaction had an actual yield equal to 60%.

EXAMPLE 2

The synthesis process of urea was carried out in the same plant described in Example 1, applying the process object of the present invention for recovering ammonia and carbon dioxide from the effluent leaving the synthesis reactor. The operating conditions of the process, where not specifically indicated, are identical to those described in Example 1.

Figure 3:
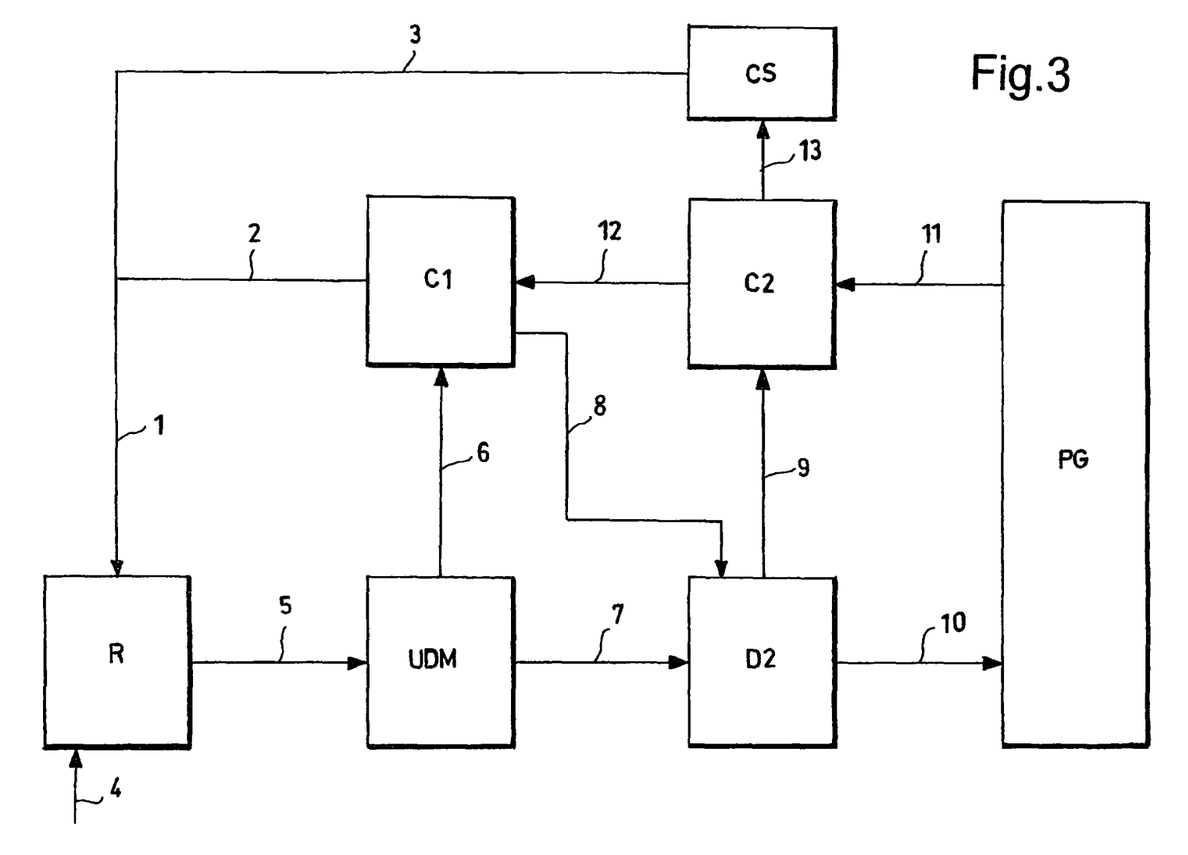
FIG. 3—schematic representation of a urea production process which uses the method object of the present invention, according to a first preferred embodiment.

The modified process is schematically illustrated in FIG. 3, in which the symbols used, when coinciding with those of FIG. 1, have the same meaning indicated in Example 1.

In the synthesis process of urea represented in FIG. 3, 2,136 tons/day of a stream 1 of ammonia and ammonia carbamate consisting of 1,518 tons/day of ammonia, 404 tons/day of carbon dioxide and 214 tons/day of water, are fed to a reactor R. The stream 1 is obtained by mixing a recycled stream 2 (1,345 tons/day) consisting of an aqueous solution of ammonium carbamate leaving a high-pressure condenser/separator C1 and a stream 3 of liquid ammonia (790.6 tons/day) substantially pure (99.91% ammonia, 0.09% water) leaving a condensation/storage section CS of ammonia. 736.3 tons/day of a stream 4 of carbon dioxide are also fed to the reactor R.

The reaction effluent 5 (2,872 tons/day) leaving the reactor R consists of a stream of ammonia (949 tons/day), carbon dioxide (404 tons/day), water vapour (515 tons/day) and urea (1,004 tons/day). The effluent 5 is fed to a distillation on hydrophobic microporous membrane unit UDM, operating under the same temperature and pressure conditions as the decomposer D1 of Example 1. The heating of the UDM unit is effected by means of an irradiation device with microwaves. The distillation is carried out under self-stripping conditions.

A first gaseous stream 6 (645 tons/day) containing ammonia (353 tons/day), carbon dioxide (270 tons/day) and water vapour (22 tons/day) leaves the UDM unit, and is fed to a high-pressure condenser/separator C1. An aqueous solution of urea 7 (2,227 tons/day) containing ammonia (596 tons/day), carbon dioxide (134 tons/day), water (515 tons/day) and urea (1,004 tons/day) leaves the bottom of the UDM unit.

The non-condensed fraction of the gaseous stream 6 is separated and fed (stream 8) to a second decomposer D2. The stream 8 (12 tons/day) consists of ammonia, carbon dioxide (1 ton/day) and is substantially free of water.

The solution of urea 7 leaving the first decomposer UDM is fed to a subsequent decomposition step of the carbamate in a decomposer D2 (medium-pressure decomposer), with the separation of a further gaseous stream 9 (705 tons/day) containing ammonia (512 tons/day), carbon dioxide (110 tons/day) and water vapour (83 tons/day), which is fed to a condenser/absorber C2 (medium-pressure condenser).

The solution comprising urea leaving the decomposer D2 stream 10 (1,534 tons/day) consists of ammonia (95 tons/day), carbon dioxide (25 tons/day), water vapour (410 tons/day) and urea (1,004 tons/day). The stream 10 is fed to the subsequent process phases schematically represented by the block PG. A stream 11 (222 tons/day) is recycled from the block PG, which is fed to the section C2 and contains ammonia (95 tons/day), carbon dioxide (25 tons/day) and water vapour (102 tons/day).

In the section C2, the gaseous stream 9 leaving the decomposer D2 is partially condensed and joined with the recycled stream 11 coming from the block PG, with the formation of a stream 12 (712.1 tons/day) containing ammonia (386 tons/day), carbon dioxide (135 tons/day) and water (191.1 tons/day). In the section C2, a stream 13 of gaseous ammonia is also separated, which is fed to the condensation/storage section CS of ammonia.

In the section C1, high-pressure condenser/separator, the gaseous stream 6 coming from the first decomposer UDM is partially condensed and joined with the stream 12, leaving the section C2, with the formation of a stream 2 (1,345 ton/day) consisting of ammonia (728 tons/day), carbon dioxide (404 tons/day) and water vapour (213 tons/day).

The use of the method, object of the present invention, allowed the selective separation of ammonia and carbon dioxide to be obtained, avoiding the formation of solid products and considerably reducing the undesired transfer of water in the form of vapour. Under these process conditions, in order to produce 1,004 tons of urea, a quantity of energy, in the form of microwave radiations, equivalent to 590 tons of saturated steam at 2.3 MPa(abs), was supplied to the UDM unit, with a saving of 54 equivalent tons with respect to the process of Example 1. In the urea synthesis reaction an actual yield equal to 65% was reached.

EXAMPLE 3

The synthesis process of urea was carried out in the same plant described in Example 1, applying the process object of the present invention for recovering ammonia and carbon dioxide from a recycled stream leaving the medium-pressure condenser. The operating conditions of the process, where not specifically indicated, are identical to those described in Example 1.

Figure 4:
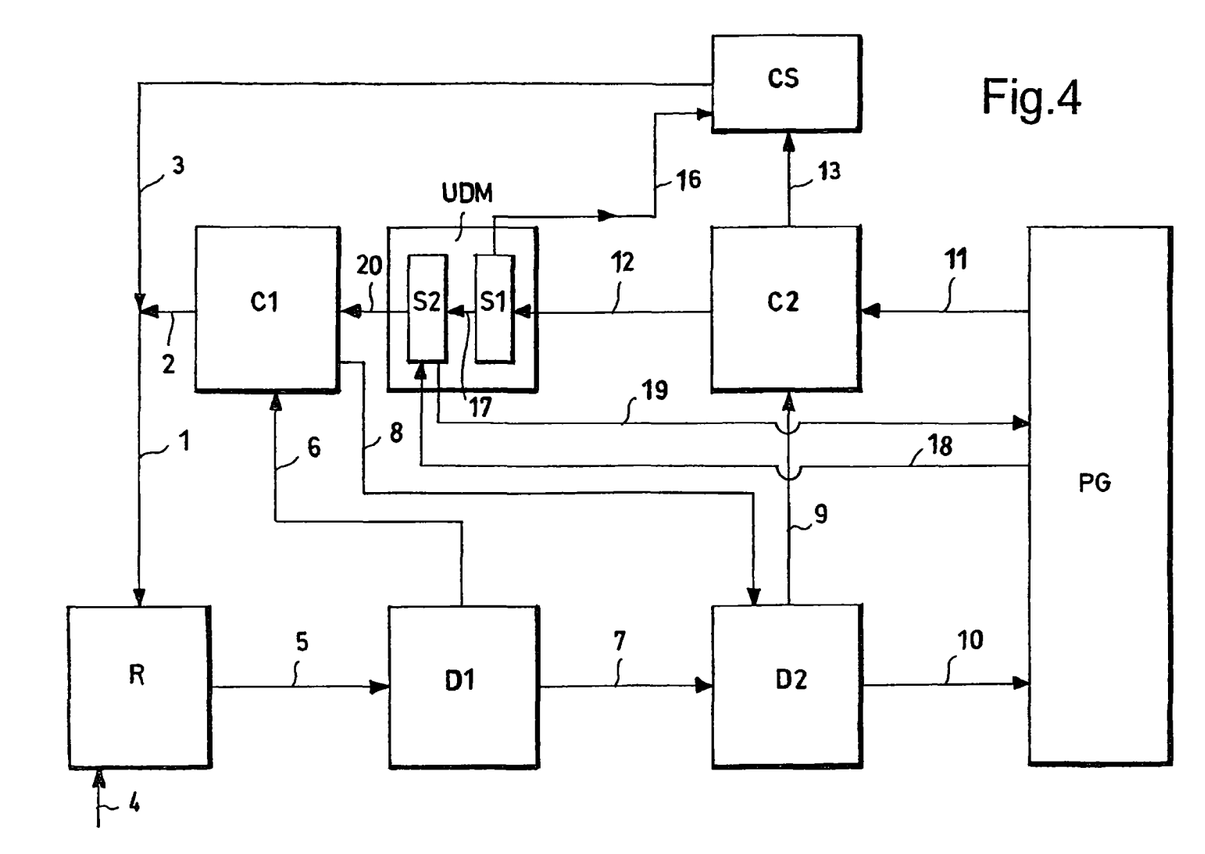
FIG. 4—schematic representation of a urea production process which uses the method object of the present invention, according to a second preferred embodiment.

The modified process is schematically illustrated in FIG. 4, in which the symbols used, when coinciding with those of FIG. 1, have the same meaning indicated in Example 1.

In the synthesis process of urea represented in FIG. 4, 1,999 tons/day of a stream 1 of ammonia and ammonia carbamate consisting of 1,520 tons/day of ammonia, 350 tons/day of carbon dioxide and 129 tons/day of water, are fed to a reactor R. The stream 1 is obtained by mixing a recycled stream 2 (774 tons/day) consisting of an aqueous solution of ammonium carbamate leaving a high-pressure condenser/separator C1 and a stream 3 of liquid ammonia (1,225 tons/day) substantially pure (99.91% ammonia, 0.09% water) leaving a condensation/storage section CS of ammonia. A stream 4 (736.3 tons/day) of carbon dioxide is also fed to the reactor R.

The reaction effluent 5 leaving the reactor R is a stream of 2,735 tons/day consisting of 951 tons/day of ammonia, 350 tons/day of carbon dioxide, 430 tons/day of water and 1,004 tons/day of urea. The reaction effluent 5 is fed to a first high-pressure decomposer D1 consisting of a falling film tube-bundle heat exchanger. In the decomposer D1, the ammonium carbamate is decomposed to ammonia and carbon dioxide creating a gaseous stream 6 (504 tons/day), which leaves the head of the decomposer D1. The above gaseous stream 6, containing ammonia (281 tons/day), carbon dioxide (205 tons/day) and water vapour (18 tons/day), is fed to a high-pressure condenser/separator C1, which operates under substantially isobar conditions with respect to those of the first decomposer D1, in order to yield its residual heat. An aqueous solution of urea 7 (2,231 tons/day) containing ammonia (670 tons/day), carbon dioxide (145 tons/day), water (412 tons/day) and urea (1,004 tons/day) leaves the bottom of the first decomposer D1. The non-condensed fraction of the gaseous stream 6 (stream 8) is fed to a second decomposer D2. The stream 8 (17 tons/day) consists of ammonia (2 tons/day), carbon dioxide (15 tons/day) and is substantially free of water.

The solution of urea 7 leaving the first decomposer D1 is fed to a subsequent decomposition step of the carbamate in the second decomposer D2 (medium-pressure decomposer). In this decomposer D2, the separation takes place of a gaseous stream 9 (750 tons/day) containing ammonia (529 tons/day), carbon dioxide (130 tons/day) and water vapour (91 tons/day), which is fed to a condenser/absorber C2 (medium-pressure condenser).

The solution comprising urea leaving the decomposer D2 stream 10 (1,498 tons/day) consists of ammonia (143 tons/day), carbon dioxide (30 tons/day), water vapour (321 tons/day) and urea (1,004 tons/day). The above stream 10 is fed to the subsequent process phases schematically represented by the block PG. A stream 11 (275 tons/day) is recycled from the block PG, which is fed to the medium-pressure condenser C2 and contains ammonia (146 tons/day), carbon dioxide (34 tons/day) and water vapour (95 tons/day).

In the medium-pressure condenser C2, the gaseous stream 9 leaving the second decomposer D2 is partially condensed and joined with the recycled stream 11 coming from the block PG, with the formation of a stream 12 (836 tons/day) consisting of an aqueous solution containing ammonia (480 tons/day), carbon dioxide (164 tons/day) and water (192 tons/day). In the section C2, a stream 13 of gaseous ammonia is also separated, which is fed to the condensation/storage section CS of ammonia.

The stream 12 leaving the medium-pressure condenser C2 is fed to a distillation on a hydrophobic microporous membrane unit UDM, consisting of a first section S1, operating at a pressure of about 2 MPa, and a second section S2, operating at a pressure of about 3 MPa. The heating of the distillation unit UDM is effected, in both sections, by microwave irradiation devices. The distillation is carried out in both sections under self-stripping conditions.

In the first section S1, a gaseous permeate stream is separated, prevalently consisting of ammonia (stream 16—460 tons/day), which is sent to the condensation/storage section CS, and a stream 17, consisting of a solution containing ammonia, carbon dioxide and water. The stream 17 leaving the first section S1 of the UDM unit is subjected to distillation on a microporous membrane in the second section S2, after mixing with a stream of water 18 (200 tons/day) coming from the block PG. Considering the behaviour of the ternary ammonia, carbon dioxide and water mixtures, the addition of a further quantity of water to the specific aqueous solution consisting of the stream 17 leaving the first section S1, allows a composition of the aqueous solution to be reached which is such that in the second section S2 a liquid stream 19 (residual aqueous solution 289 tons/day) is separated, prevalently containing water (282 tons/day) and smaller quantities of ammonia (3 tons/day) and carbon dioxide (4 tons/day), and a stream 20 (gaseous permeate stream—287 tons/day) containing most of the carbon dioxide (160 tons/day), in addition to ammonia (17 tons/day) and water (110 tons/day).

The liquid stream 19 leaving the second section S2 is recycled to the urea process phases represented by the block PG, whereas the stream 20 leaving the second section S2 of the UDM unit is fed to the high-pressure condenser/separator C1. In the above condenser/separator C1, the gaseous stream 6 coming from the decomposer D1 is partially condensed and joined with the above stream 20, with the formation of the stream 2 (774 tons/day), sent to the reactor R, consisting of ammonia (296 tons/day), carbon dioxide (350 tons/day) and water vapour (128 tons/day).

The use of the method, object of the present invention, allowed the selective separation of ammonia and carbon dioxide to be obtained, avoiding the formation of solid products and considerably reducing the undesired transfer of water in the form of vapour. Under these process conditions, in order to produce 1,004 tons of urea, a quantity of saturated water vapour 2.3 MPa (abs) equal to 550, was supplied to the first decomposer D1, with a saving of 94 tons with respect to the process of Example 1. In the urea synthesis reaction an actual yield equal to 68% was reached.

The invention claimed is:

1. An equipment, comprising:
   a distillation unit comprising a hydrophobic microporous membrane configured to operate at a temperature of 50 to 250° C. and at a pressure of 50 KPa to 20 MPa absolute;
   a feeding line connecting the distillation unit to a urea synthesis reactor; and
   a heating unit,
   wherein
   the feeding line feeds to the distillation unit an aqueous solution, which is a reaction effluent from the urea synthesis reactor comprising from 20 to 70% by weight of ammonia, from 10 to 60% by weight of carbon dioxide, from 10 to 70% by weight of water, and optionally urea;
   the distillation unit distils the aqueous solution and forms a residual aqueous solution and a permeated gaseous stream comprising ammonia carbon dioxide, and water;
   the hydrophobic microporous membrane contemporaneously recovers ammonia and carbon dioxide from the aqueous solution; and
   the heating units heats the aqueous solution.

2. The equipment of claim 1, wherein the heating unit comprises a microwave-generating device.

3. The equipment of claim 2, wherein the microwave-generating device is arranged so as to irradiate the aqueous solution in such a way that a temperature of the aqueous solution increases along a direction of a stream of the aqueous solution.

4. The equipment of claim 1, wherein the distillation unit comprises two or more sections which operate under different temperature and pressure conditions.

5. The equipment of claim 1, wherein the aqueous solution comprises urea in a content of more than 0% and equal to or less than 60% by weight.

6. The equipment of claim 1, wherein the hydrophobic microporous membrane comprises a hydrophobic polymer which forms a contact angle equal to or higher than 90 degrees with the aqueous solution.

7. The equipment of claim 1, wherein the hydrophobic microporous membrane comprises a hydrophobic polymer which forms a contact angle equal to or higher 120 degrees with the aqueous solution.

* * * * *